(12) United States Patent
Stochniol et al.

(10) Patent No.: US 10,793,488 B2
(45) Date of Patent: Oct. 6, 2020

(54) PROCESS FOR OLIGOMERIZING OLEFINS WITH STREAMS HAVING A REDUCED OLEFIN CONTENT

(71) Applicant: Evonik Operations GmbH, Essen (DE)

(72) Inventors: Guido Stochniol, Haltern am See (DE); Jörg Schallenberg, Dorsten (DE); Stephan Peitz, Oer-Erkenschwick (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 16/654,135

(22) Filed: Oct. 16, 2019

(65) Prior Publication Data
US 2020/0123080 A1  Apr. 23, 2020

(30) Foreign Application Priority Data
Oct. 19, 2018 (EP) .................................. 18201566

(51) Int. Cl.
| | | |
|---|---|---|
| *C07C 2/10* | (2006.01) | |
| *B01J 21/12* | (2006.01) | |
| *B01J 23/78* | (2006.01) | |
| *C07C 7/00* | (2006.01) | |
| *C07C 7/04* | (2006.01) | |

(52) U.S. Cl.
CPC ................ *C07C 2/10* (2013.01); *B01J 21/12* (2013.01); *B01J 23/78* (2013.01); *C07C 7/005* (2013.01); *C07C 7/04* (2013.01); *C07C 2521/04* (2013.01); *C07C 2521/08* (2013.01); *C07C 2523/04* (2013.01); *C07C 2523/755* (2013.01); *C07C 2523/78* (2013.01)

(58) Field of Classification Search
CPC .. C07C 2/10; C07C 7/005; C07C 7/04; C07C 2521/04; C07C 2521/08; C07C 2523/04; C07C 2523/755; C07C 2523/78; C07C 2/00–36; B01J 21/12; B01J 23/78; B01J 35/1023; B01J 37/0063; B01J 35/1019; B01J 23/755; B01J 37/0009; C10G 50/00; C10G 2300/1088
See application file for complete search history.

(56) References Cited

U.S. PATENT DOCUMENTS

| | | | |
|---|---|---|---|
| 9,682,898 B2 | 6/2017 | Peitz et al. | |
| 2016/0152527 A1* | 6/2016 | Peitz | C07C 5/03 549/313 |
| 2016/0312131 A1* | 10/2016 | Luebke | C07C 2/06 |
| 2019/0359748 A1* | 11/2019 | Chen | C08F 4/65908 |

FOREIGN PATENT DOCUMENTS

| | | |
|---|---|---|
| WO | 99/25668 | 5/1999 |
| WO | 2014/207034 | 12/2014 |

OTHER PUBLICATIONS

European Search Report dated Jan. 22, 2020 in European Application No. 19203314.0.

* cited by examiner

*Primary Examiner* — Ali Z Fadhel
(74) *Attorney, Agent, or Firm* — Grüneberg and Myers PLLC

(57) ABSTRACT

A process is used for oligomerizing C2- to C8-olefins in several reaction stages in which the starting mixture and the respective outputs from the reaction stages are separated and are fed to different reaction stages.

12 Claims, 1 Drawing Sheet

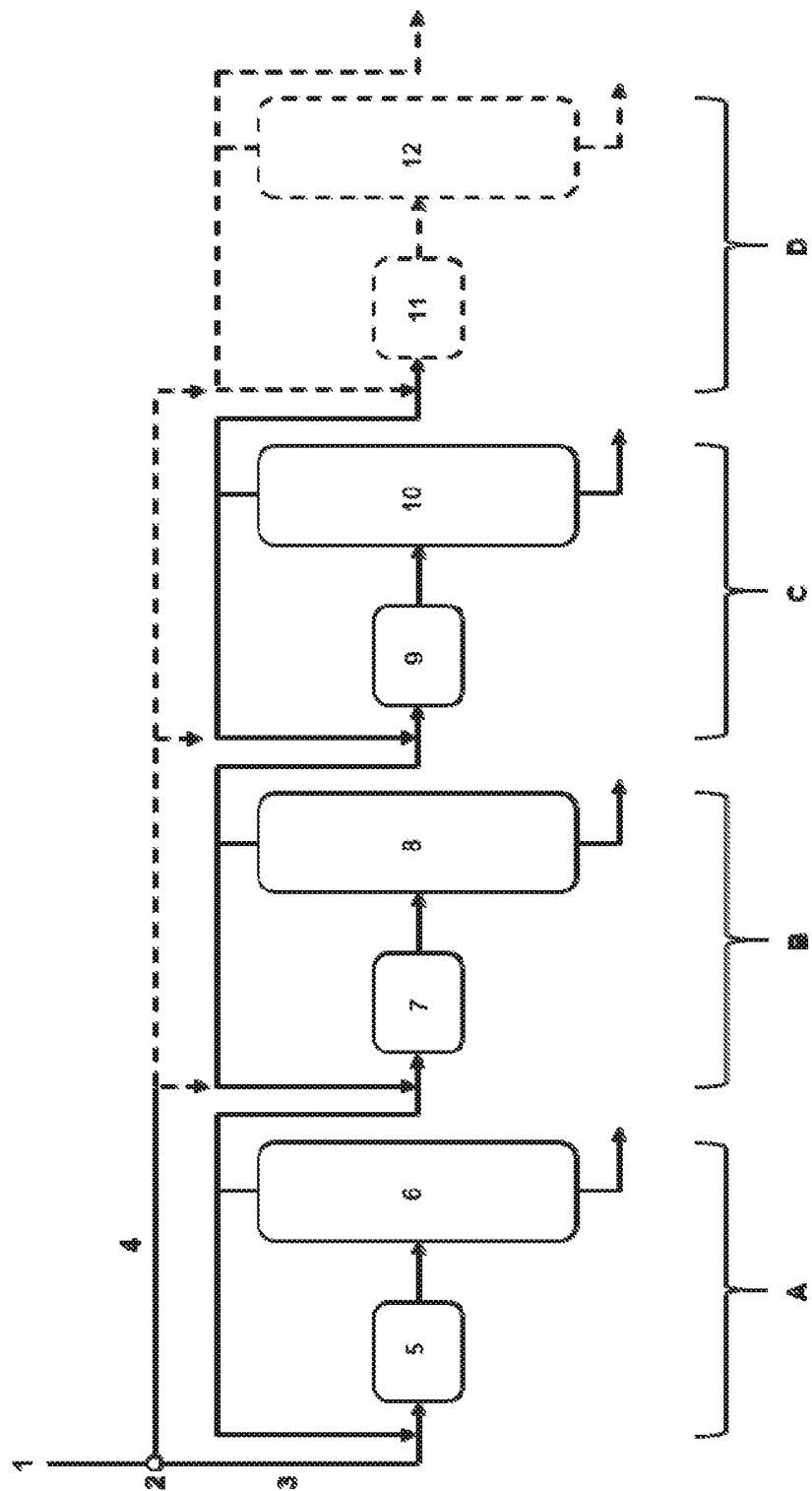

PROCESS FOR OLIGOMERIZING OLEFINS WITH STREAMS HAVING A REDUCED OLEFIN CONTENT

CROSS-REFERENCE TO RELATED APPLICATIONS

The present application claims the benefit to the European Application EP 18201566.9, filed on Oct. 19, 2018, which is incorporated by reference in its entirety.

BACKGROUND OF THE INVENTION

Field of the Invention

The present invention relates to a process for oligomerizing C2- to C8-olefins in several reaction stages in which the starting mixture and the respective outputs from the reaction stages are separated and are fed to different reaction stages.

Discussion of the Background

Oligomerization is generally understood as meaning the reaction of unsaturated hydrocarbons with themselves to form correspondingly longer-chain hydrocarbons, the so-called oligomers. Thus, for example, an olefin having six carbon atoms (hexene) can be formed by oligomerization of two olefins having three carbon atoms. The oligomerization of two molecules with one another is also referred to as dimerization.

The resulting oligomers are intermediates that are used, for example, for producing aldehydes, carboxylic acids and alcohols. The oligomerization of olefins is carried out on a large industrial scale either in the homogeneous phase using a dissolved catalyst or heterogeneously over a solid catalyst, or else with a biphasic catalyst system.

Processes for oligomerizing olefins are sufficiently well known in the related art and are used on an industrial scale. The production quantities amount to several thousand kilotons per year in Germany alone. In order to ensure highest possible conversions and as far as possible continuous operation of oligomerization processes, industrial plants usually comprise not just one, but at least two reaction stages connected in series. As a result, the oligomerization process can be kept in operation even in the case of failure of one reaction stage.

The source of the olefins for the oligomerization processes are generally steam crackers in which short-chain olefins such as ethylene or propylene but also a butadiene- and butene-containing C4-fraction (so-called crack C4) can be obtained from naphtha, which can then be freed from isobutene and then fed to an oligomerization process. Since then, the switch from naphtha as raw material for steam crackers to cheaper ethane from shale gas results in the proportion of olefins in the streams obtained being lower.

Lower olefin concentrations can however represent an economic and technical problem for further processing. Existing plants are not usually designed to be able to ensure adequately high conversions, even at low olefin concentrations, due to their original construction. In addition, the integrated distillation columns may reach their hydrodynamic limits if the proportion of inert fractions not to be oligomerized, such as alkanes, is too high. The high inert fractions also represent a negative cost contribution since these inert fractions have an unfavourable energetic effect on the overall process.

SUMMARY OF THE INVENTION

The object of the present invention was to provide a process for oligomerization of olefins which does not have the aforementioned problems. The basic object of the present invention was achieved, for example, with the process for oligomerization according to embodiment 1. Preferred configurations are specified in further embodiments.

1. Process for oligomerizing C2- to C8-olefins in at least three reaction stages connected in series, each comprising at least one reactor and at least one distillation column, wherein the method comprises the following steps:
    (a) providing a starting mixture comprising C2- to C8-olefins, and dividing the starting mixture into two feed streams, wherein one feed stream is fed as feed stream to the first reaction stage and the second feed stream is fed as feed stream to at least one of the downstream reaction stages in which the olefin content in the feed stream is less than 50% by weight;
    (b) 1st reaction stage: oligomerization, using an oligomerization catalyst, of the olefins in the feed stream to the first reaction stage in at least one reactor and separating the oligomers formed in this case as bottom product in a downstream distillation column, wherein the overhead product formed in the distillation column is at least partially fed as feed stream to the second reaction stage;
    (c) 2nd reaction stage: oligomerization, using an oligomerization catalyst, of the olefins in the feed stream to the second reaction stage in at least one reactor and separating the oligomers formed in this case as bottom product in a distillation column, wherein the overhead product formed in the distillation column is at least partially fed as feed stream to the third reaction stage;
    (d) 3rd reaction stage: oligomerization, using an oligomerization catalyst, of the olefins in the feed stream to the third reaction stage in at least one reactor and separating the oligomers formed in this case as bottom product in a distillation column;
    wherein the reactor(s) in the last reaction stage are operated adiabatically, but the reactors in the preceding reaction stages are cooled using a cooling medium; and
    wherein an oligomerization catalyst is used in the reactors of the individual reaction stages comprising a nickel compound on an aluminosilicate support material and which comprises less than 0.5% by weight titanium dioxide and zirconium dioxide in its overall composition.
2. Process for oligomerization according to embodiment 1, wherein, based on a cooling power of 100% for the reactor(s) in the first reaction stage, the cooling power in the reactor(s) of the subsequent reaction stages is less than 100% but is 0% only in the last reaction stage.
3. Process for oligomerization according to embodiment 1 or 2, wherein the heat absorbed by the cooling medium is used to heat one or more of the feed streams to the individual reaction stages.
4. Process for oligomerization according to embodiment 3, wherein the heated feed streams to the individual reaction stages have a temperature of >50° C.
5. Process for oligomerization according to any of embodiments 1 to 4, wherein the oligomerization in each of the reaction stages present is carried out at a temperature in the range of 50 to 200° C., preferably 60 to 180° C., particularly preferably in the range of 60 to 130° C.

6. Process for oligomerization according to any of embodiments 1 to 5, wherein the pressure in the oligomerization of each of the reaction stages present is 10 to 70 bar, preferably 20 to 55 bar.
7. Process for oligomerization according to any of embodiments 1 to 6, wherein the oligomerization catalyst in the reactors of the individual reaction stages has a composition of 15 to 40)/by weight NiO, 5 to 30% by weight $Al_2O_3$, 55 to 80% by weight $SiO_2$ and 0.01 to 2.5% by weight of an alkali metal oxide.
8. Process for oligomerization according to any of embodiments 1 to 7, wherein the process has 4 reaction stages and, based on embodiment 1, a modified step (d) and an additional step (e):
   (d) 3rd reaction stage: oligomerization, using an oligomerization catalyst, of the olefins in the feed stream to the third reaction stage in at least one reactor and separating the oligomers formed in this case as bottom product in a distillation column, wherein the overhead product formed in the distillation column is at least partially fed as feed stream to the fourth reaction stage; and
   (e) 4th reaction stage: oligomerization, using an oligomerization catalyst, of the olefins in the feed stream to the fourth reaction stage in at least one reactor and separating the oligomers formed in this case as bottom product in a distillation column.
9. Process for oligomerization according to embodiment 8, wherein the process has five reaction stages and, based on embodiment 8, a modified step (e) and an additional step (f):
   (e) 4th reaction stage: oligomerization, using an oligomerization catalyst, of the olefins in the feed stream to the fourth reaction stage in at least one reactor and separating the oligomers formed in this case as bottom product in a distillation column, wherein the overhead product formed in the distillation column is at least partially fed as feed stream to the fifth reaction stage; and
   (f) 5th reaction stage: oligomerization, using an oligomerization catalyst, of the olefins in the feed stream to the fifth reaction stage in at least one reactor and separating the oligomers formed in this case as bottom product in a distillation column.
10. Process for oligomerization according to any of embodiments 1 to 9, wherein the overhead product of the distillation column of the last reaction stage, i.e. the third, fourth or fifth reaction stage, is partially or fully recycled to the reactor in this reaction stage and/or is partially or fully discharged from the process.

BRIEF DESCRIPTION OF THE DRAWING

The FIGURE shows a schematic diagram of the invention with several reaction stages.

DETAILED DESCRIPTION OF THE INVENTION

The process according to the invention is a process for oligomerizing C2- to C8-olefins in at least three reaction stages connected in series, each comprising at least one reactor and at least one distillation column, wherein the method comprises the following steps:
(a) providing a starting mixture comprising C2- to C8-olefins, and dividing the starting mixture into two feed streams, wherein the one feed stream is fed as feed stream to the first reaction stage and the second feed stream is fed as feed stream to at least one of the downstream reaction stages in which the olefin content in the feed stream is less than 50% by weight:
(b) 1st reaction stage: oligomerization, using an oligomerization catalyst, of the olefins in the feed stream to the first reaction stage in at least one reactor and separating the oligomers formed in this case as bottom product in a downstream distillation column, wherein the overhead product formed in the distillation column is at least partially fed as feed stream to the second reaction stage:
(c) 2nd reaction stage: oligomerization, using an oligomerization catalyst, of the olefins in the feed stream to the second reaction stage in at least one reactor and separating the oligomers formed in this case as bottom product in a distillation column, wherein the overhead product formed in the distillation column is at least partially fed as feed stream to the third reaction stage:
(d) 3rd reaction stage: oligomerization, using an oligomerization catalyst, of the olefins in the feed stream to the third reaction stage in at least one reactor and separating the oligomers formed in this case as bottom product in a distillation column:
wherein the reactor(s) in the last reaction stage is operated adiabatically.

In the context of the present invention, the term "reaction stage" means a plant section comprising one or more reactor(s) and one or more distillation column(s) downstream of the reactor. In a preferred embodiment, only one distillation column is present per reaction stage. In the distillation columns, in particular the oligomers generated are separated from the residual output stream of the reactor which comprises, for example, alkanes and unconverted olefins. Typical process-engineering units which can be incorporated in the reaction stages, such as preheaters for the feed, heat exchangers or similar, for example, are not listed separately here but are familiar to those skilled in the art.

With the procedure described, which represents a combination of stream distribution, variable types of reactor operation and optimized process regime, a significantly more efficient utilization of the olefins present could be achieved compared to a conventional procedure, especially if the olefin content in the feed stream to one of the later reaction stages is comparatively low. If the olefin content in the feed stream to one of the later reaction stages is too low due to the consumption of olefins in the preceding reaction stage(s), conversions and space-time yields worsen. An economically problematic process regime of this kind can be prevented by the process according to the invention.

However, the process according to the invention provides not only dividing the starting mixture provided in step (a) but also the adiabatic operating mode of the reactor(s) in the last reaction stage. The expression "adiabatically operated" is to be understood to mean that the reactor(s) in the last reaction stage are not actively cooled. Instead, the heat released during the oligomerization is carried from the reactor with the product stream, wherein less energy is required for evaporation in the downstream distillation column and the distillation can thus be carried out with saving of energy.

The process according to the invention comprises at least three reaction stages. In a preferred embodiment, the process for oligomerization comprises at maximum five reaction stages. Particularly preferred is a process regime with four or five reaction stages. Each of these reaction stages, independently of one another, comprises one or more reactors and one or more downstream distillation columns in order to separate the oligomers formed from the residual output stream from the reactor. It is also conceivable, however, that one of the reaction stages comprises two or more reactors, whereas in a preceding or subsequent reaction stage only one reactor is present.

If 4 reaction stages are present, the process according to the invention mentioned above with a modified step (d) and an additional step (e) is carried out as follows, wherein the steps (a) to (c) remain unchanged as described:

(d) 3rd reaction stage: oligomerization, using an oligomerization catalyst, of the olefins in the feed stream to the third reaction stage in at least one reactor and separating the oligomers formed in this case as bottom product in a distillation column, wherein the overhead product formed in the distillation column is at least partially fed as feed stream to the fourth reaction stage: and (e) 4th reaction stage: oligomerization, using an oligomerization catalyst, of the olefins in the feed stream to the fourth reaction stage in at least one reactor and separating the oligomers formed in this case as bottom product in a distillation column.

If 5 reaction stages are present, the process according to the invention with 4 reaction stages mentioned above with a modified step (e) and an additional step (f) is carried out as follows, wherein the steps (a) to (d) remain unchanged as described:

(e) 4th reaction stage: oligomerization, using an oligomerization catalyst, of the olefins in the feed stream to the fourth reaction stage in at least one reactor and separating the oligomers formed in this case as bottom product in a distillation column, wherein the overhead product formed in the distillation column is at least partially fed as feed stream to the fifth reaction stage; and (f) 5th reaction stage: oligomerization, using an oligomerization catalyst, of the olefins in the feed stream to the fifth reaction stage in at least one reactor and separating the oligomers formed in this case as bottom product in a distillation column.

The process according to the invention can be carried out broadly as follows: The starting point is the provision of a starting mixture comprising C2- to C8-olefins. The starting mixture is divided into two feed streams prior to the feed to the first reaction stage. The splitting can be carried out in a manner known to those skilled in the art, for example by means of a pipeline diverting from the main pipeline (for the first feed stream). The stream can be separated, for example, via a mass regulator. One (first) feed stream is passed as feed stream to the first reaction stage, whereas the other (second) feed stream is passed, depending on the olefin content in the feed stream, to one of the downstream reaction stages. The feed stream to the downstream reaction stages, i.e. to the second and further reaction stages, is fed at least partially from the overhead product of the distillation column of the respective preceding reaction stage. If the olefin content in the feed stream to one of the subsequent reaction stages is less than 50% by weight, at least a portion of the second feed stream is additionally metered in in order to increase the proportion of olefins in the feed stream.

In the individual reaction stages, the respective feed stream is oligomerized in accordance with the invention in the at least one reactor and the oligomerizate obtained is passed in each case to a distillation column in which the oligomers formed are separated as bottom product from the residual output stream of the reactor, comprising at least alkanes and unreacted olefins as overhead product. Depending on the reaction stage, the overhead product is then passed at least partially as feed stream to the respective next reaction stage and optionally partially recycled to the reactor of the respective reaction stage. In the last reaction stage, i.e. the third, fourth, fifth or subsequent reaction stage, the overhead product of the distillation column can be partially recycled to the reactor in the same reaction stage and partially discharged from the process. If the overhead product of the distillation column of the last reaction stage is discharged from the process disclosed here, this can serve as synthetic raw material for further processes (e.g. hydroformylation, C-source for light arc in acetylene production), as combustion gas or as a propellant gas after full hydrogenation to alkanes, as cooking gas and the like.

Olefins employed for the process according to the invention include C2- to C8-olefins, preferably C2- to C6-olefins, more preferably C3- to C5-olefins, or olefin mixtures based thereon, which may also contain proportions of analogous alkanes. Suitable olefins are, inter alia, α-olefins, n-olefins and cycloalkenes, preferably n-olefins. In a preferred embodiment, the olefin is n-butene.

The olefins are typically not used as reactants in pure form, but in available technical-grade mixtures. The term starting mixture used additionally in this invention is therefore to be understood as encompassing any type of mixtures containing the relevant olefins to be oligomerized in an amount which makes it possible to perform the oligomerization economically. The starting mixtures used in accordance with the invention preferably contain practically no further unsaturated compounds and polyunsaturated compounds such as dienes or acetylene derivatives. It is preferable to employ starting mixtures containing less than 5% by weight, in particular less than 2% by weight, of branched olefins based on the olefin proportion.

Propylene is produced on a large industrial scale by cracking of naphtha and is a commodity chemical which is readily available. C5-olefins are present in light petroleum fractions from refineries or crackers. Technical mixtures which contain linear C4-olefins are light petroleum fractions from refineries, C4-fractions from FC crackers or steam crackers, mixtures from Fischer-Tropsch syntheses, mixtures from the dehydrogenation of butanes, and mixtures formed by metathesis or from other industrial processes. Mixtures of linear butenes suitable for the process according to the invention are obtainable for example from the C4-fraction of a steam cracker. Butadiene is removed in the first step here. This is accomplished either by extraction (distillation) of the butadiene or by selective hydrogenation thereof. In both cases a virtually butadiene-free C4-cut is obtained, the so-called raffinate I. In the second step, isobutene is removed from the C4-stream, for example by production of MTBE by reaction with methanol. The now isobutene-free and butadiene-free C4-cut, the so-called raffinate II, contains the linear butenes and any butanes. If at least some of the 1-butene obtained is removed therefrom, the so-called raffinate III is obtained.

In a preferred embodiment in the process according to the invention, C4-olefin-containing streams are fed as starting mixture. Suitable olefin mixtures are particularly raffinate I and raffinate II and raffinate III.

All reactors known to those skilled in the art can be used as reactor for the respective reaction stages which are suitable for oligomerization, for example tubular reactors, tube bundle reactors, settler-riser reactors, slurry reactors. Preference is given to tubular reactors and/or tube bundle reactors. If a reaction stage has two or more reactors, the reactors can be the same or different from one another. The reactors in a reaction stage may also vary in their construction or their configuration. The first reactor in a reaction stage may have, for example, a larger volume than the subsequent reactor in the same reaction stage. It is also possible that the reactors in the individual reaction stages are the same or different from one another. It is also possible here that the reactors in the individual reaction stages are different in their construction or their configuration. The reactor in the first reaction stage may have, for example, a larger volume than one or all reactors in the downstream reaction stages.

The one reactor or the reactors of the individual reaction stages contain in each case an oligomerization catalyst for carrying out the oligomerization, especially a heterogeneous oligomerization catalyst. The oligomerization catalyst in this case is particularly in the form of granules, an extrudate or in tablet form.

The (heterogeneous) oligomerization catalysts comprise a nickel compound, preferably nickel oxide, on an aluminosilicate support material, but comprise less than 0.5% by weight, preferably less than 0.1% by weight, particularly preferably less than 0.01% by weight titanium dioxide and zirconium dioxide, based on the total composition of the oligomerization catalyst. The support material can be an amorphous, mesoporous aluminosilicate, a crystalline, microporous aluminosilicate or an aluminosilicate having amorphous and crystalline phases. In the context of the present invention, "amorphous" is to be understood as meaning the property of a solid which results from the fact that the solid has no crystal structure. i.e. no long-range order, in contrast to crystalline solids.

Further preferred in accordance with the invention, the oligomerization catalyst has a composition of 15% to 40% by weight, preferably 15% to 30% by weight NiO, 5% to 30% by weight $Al_2O_3$, 55% to 80% by weight $SiO_2$ and 0.01% to 2.5% by weight, preferably 0.05% to 2% by weight, of an alkali metal oxide, preferably sodium oxide. The FIGURE is based on a total composition of 100% by weight. The oligomerization catalyst is substantially free from titanium dioxide and zirconium dioxide, the oligomerization catalyst in particular comprising less than 0.5% by weight, preferably less than 0.1% by weight, particularly preferably less than 0.01% by weight titanium dioxide and zirconium dioxide in its total composition.

The oligomerization catalyst preferably has a specific surface area (calculated according to BET) of 150 to 700 $m^2/g$, more preferably 190 to 600 $m^2/g$, particularly preferably 220 to 550 $m^2/g$. The BET surface area is measured by nitrogen physisorption according to DIN ISO 9277 (2014-01 version).

The oligomerization catalyst present in the individual reactors in the reaction stages may be selected in each case independently of one another from the aforementioned substances. The individual oligomerization catalysts in the reactors are not always exactly identical here, but differ from each other in the composition, possibly only to a limited extent. This is also due to the fact that even if at the time point of the first start-up of the process according to the invention each reactor contains a fully identical catalyst composition, this composition changes with time during operation by the widest variety of effects over the course of the years (regenerated catalyst behaves differently to freshly produced catalysts, abrasion during operation, different ageing rates and/or poisoning, etc.).

An oligomerization catalyst can be produced by the known process of impregnation, wherein the support material is charged with a solution of a transition metal compound, especially a nickel compound, and is then calcined, or coprecipitation in which the entire catalyst composition is precipitated from a single, mostly aqueous solution. The oligomerization catalyst can also be produced by other processes familiar to those skilled in the art.

The oligomerization can be carried out in each of the reaction stages present at a temperature in the range of 50 to 200° C., preferably 60 to 180° C., preferably in the range of 60 to 130° C. The pressure of each of the reaction stages present can be from 10 to 70 bar, preferably 20 to 55 bar. In a preferred embodiment of the present invention, the oligomerization is carried out in each reaction stage in the liquid phase. If the oligomerization is to be carried out in the liquid phase the parameters pressure and temperature must to this end be chosen such that the reactant stream (the employed olefins or olefin mixtures) is in the liquid phase.

The weight-based space velocities (reactant mass per unit catalyst mass per unit time: weight hourly space velocity (WHSV)) are in the range between 1 g of reactant per g of catalyst and per h (=1 $h^{-1}$) and 190 $h^{-1}$, preferably between 2 $h^{-1}$ and 35 $h^{-1}$, particularly preferably between 3 $h^{-1}$ and 25 $h^{-1}$.

Particularly when using a catalyst comprising a nickel compound, preferably nickel oxide, on an aluminosilicate support, the degree of dimerization (also referred to as "percentage selectivity based on dimerization") after the oligomerization, based on the converted reactant, is at least 60%, more preferably at least 75%, particularly preferably at least 80%.

The oligomerization of olefins is an exothermic reaction, i.e. a reaction in which heat is released. In order to keep the oligomerization temperature in a desired range, the reactors can be cooled in order to remove some or all of the heat released. In order to utilize the heat released for subsequent processes, cooling can be partly completely dispensed with, as is the case in the final reaction stage. The heat released during the oligomerization is removed from the reactor by means of the output of the product stream and is used in the distillation column to the extent that less energy has to be provided in order to achieve the desired separation effect in the distillation.

In a preferred embodiment, all reactors in the preceding reaction stages are cooled except for the final reaction stage. In this case, a cooling medium known to those skilled in the art, cooling water for example, can be used. In a preferred embodiment, temperature increase in the reactor despite cooling should not exceed 5 K. This corresponds to an isothermal operating mode of the reactors. Based on a cooling power of 100% for the reactor(s) in the first reaction stage, the cooling power in the reactor(s) of the subsequent reaction stages is less than 100% but is not 0% except in the last reaction stage.

In an especially preferred embodiment, in the presence of three reaction stages, the cooling power for the reactor(s) of the first reaction stage is 100% and for the reactor(s) of the second reaction stage is 10 to 60%, wherein the reactor of the third and final reaction stage is operated adiabatically. In a further especially preferred embodiment, in the presence of four reaction stages, the cooling power for the reactor(s) of the first reaction stage is 100%, for the reactor(s) of the second reaction stage is 40 to 60% and for the reactor(s) of the third reaction stage 10 to 30%, wherein the reactor of the fourth and final reaction stage is operated adiabatically.

The heat absorbed by the cooling medium during the cooling in the reaction stages preceding the adiabatically operated reaction stage can be used in a preferred embodiment to heat one or more feed streams, preferably all feed streams, to the individual reaction stages, preferably to a temperature T>50° C. This can be carried out in a manner known to those skilled in the art, particularly by using a heat exchanger. Thus, the heat formed during the reaction and absorbed by the cooling medium during cooling can still be used for the further process, which is advantageous from an economic and ecological point of view.

The linearity of an oligomerization product or of the dimers formed is described by the ISO index and represents a value for the average number of methyl branches in the dimer.

For example (for butene as the reactant), n-octenes contribute 0, methyl heptenes contribute 1 and dimethyl hexenes contribute 2 to the ISO index of a C8 fraction. The lower the ISO index, the more linear the construction of the molecules in the respective fraction. The ISO index is calculated according to the following general formula, wherein the proportion of the individual dimer fractions refers to the total dimer fraction:

$$\frac{\left(\begin{array}{l}\text{singly branched dimers (\% by weight)}+\\ 2\times\text{two-fold branched dimers (\% by weight)}\end{array}\right)}{100}$$

Accordingly, a dimer mixture having an ISO index of 1.0 has an average of exactly 1 methyl branch per dimeric molecule.

The ISO index of the product from the oligomerization process according to the invention is preferably 0.8 to 1.2, more preferably 0.8 to 1.15.

The oligomers produced by the process according to the invention are utilized inter alia for producing aldehydes, alcohols and carboxylic acids. Thus for example the dimerizate of linear butenes affords a nonanal mixture by hydroformylation. This provides either the corresponding carboxylic acids by oxidation or a C9-alcohol mixture by hydrogenation.

The C9 acid mixture may be used for producing lubricants or siccatives. The C9-alcohol mixture is a precursor for the production of plasticizers, particularly dinonyl phthalates, or DINCH.

FIGURE shows an embodiment corresponding to the present invention. Starting stream (1) is firstly divided at point (2) into the feed stream to the first reaction stage (3) and the feed stream to at least one of the downstream reaction stages having an olefin content of less than 50% (4). Feed stream (3) is then fed to reactor (5) of the first reaction stage (A) and the oligomerizate obtained from the reactor is fed to the distillation column (6), where the oligomers formed are separated off as bottom product. The overhead product is partially fed back to reactor (5) and partially to the next, second reaction stage (B). Optionally, i.e. if the olefin content in the second stage is already below 50% in the feed, the feed stream (4) separated off from the starting stream can already be metered in to the second reaction stage (B). Therein, oligomerization is firstly effected in a reactor (7). The oligomerizate obtained arrives at distillation column (8), where the oligomers formed in reactor (7) of the second reaction stage (B) are separated off via the bottoms. The overhead product is partially fed to reactor (7) and partially to the third reaction stage (C). Therein, the feed stream is subjected to an oligomerization in reactor (9) and the oligomers separated off as bottom product in distillation column (10). A portion of the overhead product is recycled to reactor (9). The feed stream (4) separated from the starting stream can be additionally fed here to the recycled overhead product (dashed arrow). The fourth reaction stage (D) is optional and therefore represented by dashed lines. The optional fourth reaction stage likewise comprises a reactor (11) and a distillation column (12). In the embodiment with 4 reaction stages, the feed stream can be fed to the third and/or fourth reaction stage. The embodiment with 5 reaction stages is not shown in the FIGURE, but the setup shown will then merely comprise a further reaction stage after reaction stage (D).

The invention claimed is:

1. A process for oligomerizing C2- to C8-olefins in at least three reaction stages connected in series, each reaction stage comprising at least one reactor and at least one distillation column, wherein the process comprises:
   (a) providing a starting mixture comprising C2- to C8-olefins, and dividing the starting mixture into first feed stream and second feed stream, wherein the first feed stream is fed as feed stream to the first reaction stage and the second feed stream is added to the feed stream to at least one of the downstream reaction stages, in which the olefin content is less than 50% by weight;
   (b) a first reaction stage: oligomerizing, using an oligomerization catalyst, the olefins in the feed stream to the first reaction stage in at least one reactor and separating oligomers formed as bottom product in a downstream distillation column, wherein an overhead product formed in the distillation column is at least partially fed as feed stream to the second reaction stage;
   (c) a second reaction stage: oligomerizing, using an oligomerization catalyst, the olefins in the feed stream to the second reaction stage in at least one reactor and separating oligomers formed as bottom product in a distillation column, wherein an overhead product formed in the distillation column is at least partially fed as feed stream to the third reaction stage; and
   (d) a third reaction stage: oligomerizing, using an oligomerization catalyst, the olefins in the feed stream to the third reaction stage in at least one reactor and separating oligomers formed in this case as bottom product in a distillation column;
   wherein the at least one reactor in the last reaction stage is operated adiabatically, but the reactors in the preceding reaction stages are cooled using a cooling medium; and
   wherein each oligomerization catalyst used in the reactors of the individual reaction stages comprises a nickel compound on an aluminosilicate support material and which comprises less than 0.5% by weight titanium dioxide and zirconium dioxide in an overall composition of each of the oligomerization catalysts.

2. The process according to claim 1, wherein, based on a cooling power of 100% for the at least one reactor in the first reaction stage, the cooling power in the reactor(s) of the subsequent reaction stages is less than 100% but is 0% only in the last reaction stage.

3. The process according to claim 1, wherein heat absorbed by the cooling medium is used to heat one or more of the feed streams to the individual reaction stages.

4. The process according to claim 3, wherein the one or more feed streams to the individual reaction stages are heated to a temperature of >50° C.

5. The process according to claim 1, wherein the oligomerization in each of the reaction stages present is carried out at a temperature in the range of 50 to 200° C.

6. The process according to claim 5, wherein the temperature is in the range of 60 to 130° C.

7. The process according to claim 1, wherein the pressure in the oligomerization of each of the reaction stages present is 10 to 70 bar.

8. The process according to claim 7, wherein the pressure is 20 to 55 bar.

9. The process according to claim 1, wherein the oligomerization catalyst in the reactors of the individual reaction stages has a composition of
15 to 40% by weight NiO,
5 to 30% by weight $Al_2O_3$,
55 to 80% by weight $SiO_2$ and
0.01 to 2.5% by weight of an alkali metal oxide.

10. The process for oligomerization according to claim 1, wherein (d) is:
(d) third reaction stage: oligomerizing, using the oligomerization catalyst, the olefins in the feed stream to the third reaction stage in at least one reactor and separating oligomers formed as bottom product in a distillation column, wherein an overhead product formed in the distillation column is at least partially fed as feed stream to the fourth reaction stage; and
wherein said process further comprises:
(e) fourth reaction stage: oligomerizing, using an oligomerization catalyst, the olefins in the feed stream to the fourth reaction stage in at least one reactor and separating oligomers formed as bottom product in a distillation column.

11. The process for oligomerization according to claim 10,
wherein (e) is:
(e) fourth reaction stage: oligomerizing, using the oligomerization catalyst, the olefins in the feed stream to the fourth reaction stage in at least one reactor and separating oligomers formed as bottom product in a distillation column, wherein the overhead product formed in the distillation column is at least partially fed as feed stream to the fifth reaction stage; and
wherein said process further comprises:
(f) fifth reaction stage: oligomerizing, using the oligomerization catalyst, of the olefins in the feed stream to the fifth reaction stage in at least one reactor and separating oligomers formed as bottom product in a distillation column.

12. The process according to claim 1, wherein the overhead product of the distillation column of the last reaction stage is partially or fully recycled to the at least one reactor in the last reaction stage and/or is partially or fully discharged from the process.

* * * * *